United States Patent [19]

Batchelder et al.

[11] Patent Number: 5,177,559
[45] Date of Patent: Jan. 5, 1993

[54] DARK FIELD IMAGING DEFECT INSPECTION SYSTEM FOR REPETITIVE PATTERN INTEGRATED CIRCUITS

[75] Inventors: John S. Batchelder, Somers; Marc A. Taubenblatt, Pleasantville, both of N.Y.

[73] Assignee: International Business Machines Corporation, Armonk, N.Y.

[21] Appl. No.: 701,936

[22] Filed: May 17, 1991

[51] Int. Cl.⁵ .......................................... G01N 15/02
[52] U.S. Cl. ..................................... 356/237; 356/338
[58] Field of Search ............................. 356/338, 237

[56] References Cited

U.S. PATENT DOCUMENTS

| | | | |
|---|---|---|---|
| 3,813,173 | 5/1974 | Teter | 356/239 |
| 3,972,616 | 8/1976 | Minami et al. | 356/237 |
| 4,153,336 | 5/1979 | Minami et al. | 356/239 |
| 4,197,011 | 4/1980 | Hudson | 356/237 |
| 4,441,124 | 4/1984 | Heebner et al. | 356/237 |
| 4,449,818 | 5/1984 | Yamaguchi et al. | 356/237 |
| 4,595,289 | 6/1986 | Feldman et al. | 356/237 |
| 4,601,577 | 7/1986 | Gotou et al. | 356/237 |
| 4,772,126 | 9/1988 | Allemand et al. | 356/337 |
| 4,806,774 | 2/1989 | Lin et al. | 356/237 |
| 4,893,932 | 1/1990 | Knollenberg . | |
| 4,895,446 | 1/1990 | Maldori et al. | 356/336 |
| 4,947,413 | 8/1990 | Jewell et al. . | |
| 4,993,837 | 2/1991 | Oshida et al. | 356/401 |
| 5,046,847 | 9/1991 | Nakata et al. | 356/237 |

FOREIGN PATENT DOCUMENTS 0028774 5/1981 European Pat. Off. .
2321532 11/1984 Fed. Rep. of Germany .
608705 1/1985 Japan .

OTHER PUBLICATIONS

Knollenberg, The Importance of Media Refractive Index in Evaluating Liquid and Surface Microcontamination Measurements, 1986, p. 501.
Nakata & Nobuyuki, Particle Detection for Patterned Wafers Using Hybrid Optical-Digital Image Processing; Nov. 1989, p. 2396.
Heinz, Robert A. et al. "Tool and Product Inspection by Optical Spatial Filtering of Periodic Images," Western Electric Engineering, vol. 17, No. 3, Jul. 1973.
Watkins, L. S. "Inspection of Integrated Circuit Photomasks with Intensity Spatial Filters," Proceedings of the I.E.E.E., vol. 57, No. 9, Sep. 1969.
Axel Rod, Norman N. Proceedings of the I.E.E.E., Apr. 1972, p. 447.
Grosewald, P. S., et al. "Automatic Detection of Defects on Wafers", IBM Technical Disclosure Bulletin vol. 21, No. 6, Nov. 1978.
Patrick, W. J., et al. "Surface Defect Analyzer", IBM Technical Disclosure Bulletin, vol. 16, No. 8, Jan. 1974.

Primary Examiner—Richard A. Rosenberger
Attorney, Agent, or Firm—Ratner & Prestia

[57] ABSTRACT

An optical inspection system for patterned semiconductor wafers generates a dark field image of the wafer by applying a collimated beam of monochrome light at an incident angle with respect to the surface of the wafer of between 8° and a maximum angle defined by the numerical aperture of the imaging system and collecting the light which is scattered at angles approximately normal to the surface of the wafer and within the numerical aperture of the imaging system. In addition, the incident light is at an angle of 45° in the surface plane of the wafer with respect to the rectangular lines which predominate in the pattern. Before forming the dark field image, the collected light is passed through a Fourier transform filter which substantially attenuates spatial frequency components corresponding to the pattern. In the resultant dark field image, defects in the pattern and contaminating particles are accentuated relative to the pattern features.

16 Claims, 5 Drawing Sheets

DARK FIELD IMAGING DEFECT INSPECTION SYSTEM FOR REPETITIVE PATTERN INTEGRATED CIRCUITS

BACKGROUND

The present invention concerns apparatus and a method for locating defects in items having regular patterns and in particular to a dark field imaging technique which may be used to inspect semiconductor wafers having fine repetitive patterns.

The detection of particles and defects on patterned wafers is a problem critical to the semiconductor industry. Contaminating particles on the surface of a semiconductor wafer can result in unintended conduction paths in the integrated circuits formed on the wafer. Defects in one or more of the photolithographic patterns which are used to produce the integrated circuits can produce non-functioning or substandard devices. It is important to identify the type and characteristics of any defects in the integrated circuits at various processing stages so that the cause of the defect can be corrected before it can adversely affect yield.

In the prior art, there are many ways to locate defects and contaminating particles on the surface of a semiconductor wafer. Generally, these methods fall into one of three classes: spatially filtered bright field imaging techniques, image analysis of bright field images and low-angle dark field imaging techniques.

One such prior art reference in U.S. Pat. No. 4,771,468 entitled SYSTEM FOR AUTOMATIC INSPECTION OF PERIODIC PATTERNS is characteristic of a bright field inspection technique that recognizes particles and pattern defects through image processing of the bright field image (without spatial filtering). The basis of the algorithm is to compare corresponding picture elements (pixels) from supposedly identical array elements on the circuit. If the center pixel matches the corresponding left and right pixels, there is no defect. Additional processing is used to test for instabilities which may occur when pixels are located next to lines or on rough surfaces, when there is interfering noise from the camera or when there are systematic changes in the optical properties of the parts being inspected. While the information produced by such a system is essentially the same as that produced by the disclosed embodiments of the present invention, an important difference is the system described in the referenced patent is relatively more expensive (because of the electronic image analyzer) and relatively slow (depending on the sophistication of the image analyzer).

Another system is described in U.S. Pat. No. 4,806,774 entitled INSPECTION SYSTEM FOR ARRAY OF MICROCIRCUIT DIES HAVING REDUNDANT CIRCUIT PATTERNS, which is hereby incorporated by reference for its teachings on optics and the inspection of semiconductor wafers. This system uses a Fourier transform lens and an inverse Fourier transform lens positioned along an optical axis.

The system forms a bright-field image of an area on the wafer at a distant image plane. In this system, spatial frequencies corresponding to the repetitive pattern are selectively attenuated in the bright-field image by inserting a spatial filter at a Fourier transform plane between the two lenses. The resulting image accentuates irregularities on the surface of the integrated circuit, such as may result from contaminating particles or from defects in the pattern.

In this system, however, the wafer is illuminated through the Fourier transform lens. Thus, light scattered and reflected by the lens is added to the image, increasing the level of background illumination. In addition, the relatively strong zero-order reflection from the wafer also passes through the Fourier transform lens producing additional background illumination. To effectively block the illuminated pattern, the Fourier spatial filter used in this system is optically dense. This reduces the amount of light passing through the filter. The combination of all of these effects reduces the sensitivity of the defect detection system.

An example of the other type of defect detection system is given in U.S. Pat. No. 4,772,126 entitled PARTICLE DETECTION METHOD AND APPARATUS, which is hereby incorporated by reference for its teachings on optics and the inspection of semiconductor wafers.

In the system described by this patent, a semiconductor wafer is illuminated at a grazing angle of incidence, between 0° and 5° of the wafer surface. The illuminating beam is oriented to strike the wafer at an angle of approximately 45° with respect to the lines of the rectangular pattern. In addition, the beam is scanned across the surface of the wafer using a scanning galvanometer. Light reflected at angles approximately normal to the surface of the wafer is collected by a video camera positioned above the wafer.

This is a conventional grazing angle configuration, the beam preferentially illuminates particles which extend above the surface of the wafer. The light reflected by these particles is collected by the camera. Particles which extend a greater distance above the surface receive a greater level of illumination, since the surface of the wafer acts as a mirror for this low angle incident radiation. In addition, this patent suggests the use of a Fourier spatial filter to attenuate spatial frequencies, corresponding to the repetitive pattern, from the image collected by the video camera.

While this system works well for detecting particles above the surface of the wafer, it is not as efficient for detecting smaller particles, which may be imbedded in surface features of the wafer, or errors in the repetitive pattern. Since these features are at or slightly below the surface of the wafer, they are not illuminated by the low angle beam and, so, will not appear in the dark field image.

In addition, since the illuminating beam is scanned across the surface of the wafer, the spatial frequency components oscillate in position at the scanning frequency in the Fourier plane. Consequently, a Fourier filter which blocks these spatial frequencies must be opaque over a larger area than if the beam is not scanned. A filter of this type would necessarily decrease the difference in illumination between small particles and defects on one hand and the background illumination levels on the other hand. This decreased difference results in a reduction in the sensitivity of the device to this type of defect when a Fourier spatial filter is used.

SUMMARY OF THE INVENTION

The present invention is embodied in a dark field inspection system in which an item having a repetitive pattern is illuminated by a beam of monochrome light at an incident angle with respect to the wafer surface of between 8° and a maximum angle as determined by the imaging lens system. This angle being limited by the constraint that the inspection system produces a dark field image. Light scattered at angles approximately normal to the surface is collected by a lens system which spatially filters the collected light to substantially attenuate spatial frequency components corresponding to the repetitive pattern. The remaining light is focused, by the lens system to form an image in which particles and defects in the repetitive pattern are accentuated.

DETAILED DESCRIPTION OF THE EXEMPLARY EMBODIMENTS

Overview

Figure 1:
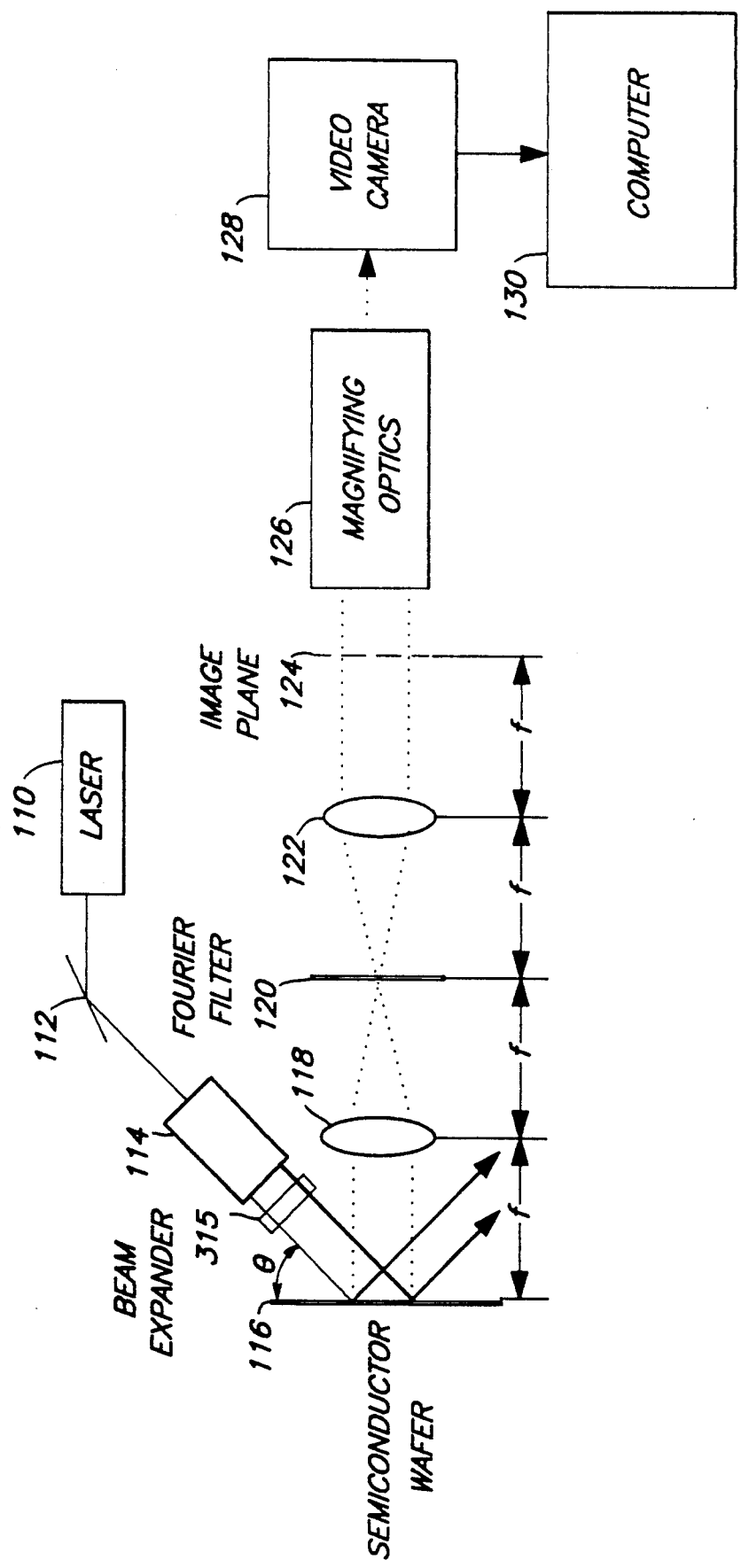
FIG. 1 is a block diagram of a wafer inspection system which includes an embodiment of the invention.

An inspection system according to the present invention employs a combination of dark-field imaging and Fourier spatial filtering to detect large and small contaminating particles as well as pattern defects in items, such as semiconductor wafers, which exhibit fine-featured repetitive patterns. The principles of Fourier spatial filtering are described in a paper by L. S. Watkins entitled "Inspection of Integrated Circuit Photomasks with Intensity Spatial Filters" *Proceedings of the IEEE* vol 57, no 9, 9/69, which is hereby incorporated by reference.

While this system is described in the context of a semiconductor wafer inspection system, it is contemplated that it may be used for inspecting other items having repetitive patterns, such as photolithographic masks, used to manufacture semiconductor devices. It may also be used to inspect liquid crystal devices, or shadow masks for color cathode ray tubes.

In the exemplary embodiments of the invention, the patterned semiconductor wafer is illuminated by a monochrome light source, such as the laser 110, at an incident angle $\theta$ with respect to the surface plane of the wafer. This angle is selected to illuminate the wafer sufficiently so that the pattern may be inspected but to prevent the low spatial frequency components of the pattern (i.e. those components closest to the specularly reflected beam) from entering the imaging system.

In addition, the angle, $\Phi$, in the plane of the pattern, which the incident light makes with respect to the rectangular features in the pattern, is selected to further reduce the intensity of the light scattered from the pattern features. For a pattern having predominantly rectangular features, an angle $\Phi$ of 45° has been found to minimize the intensity of the light scattered from the pattern features.

This normal scattered light is collected by an optical system which includes a spatial filter 120 to produce a dark field image. That is to say an image in which the background appears dark and the surface features of interest are illuminated.

The spatial filter is selected to strongly attenuate the spatial frequency components resulting from the pattern which do enter the optical imaging system. The filtered light is then focused into an image which is captured by a video camera 128 for analysis by a computer 130. The computer executes algorithms which discriminate and analyze the defects to determine their characteristics and size.

Three different optical systems are illustrated in the various embodiments of the invention. The first employs standard Fourier transform and inverse Fourier transform lenses together with the Fourier spatial filter to generate the filtered image. The second embodiment uses a 1:1 lens as an objective. This lens, coupled with the Fourier spatial filter, also attenuates the spatial frequency components of the dark field image. The third embodiment uses a standard infinity corrected microscope objective lens, an afocal relay lens and a tube lens in conjunction with the Fourier filter to both magnify the dark field image collected from the wafer and to spatially filter the image to accentuate any defects in the pattern.

DETAILED DESCRIPTION

The first exemplary embodiment of the invention is shown in FIG. 1. In this FIGURE and in FIGS. 2 and 3, the path of the scattered light is illustrated by ray tracing. The traced rays are shown as dotted lines. These lines represent the path of diffracted collimated light; they do not represent points on the object being imaged. This representation is used to more clearly illustrates the spatial filtering of the light.

In all of the exemplary embodiments a conventional helium-neon laser 110 produces a collimated beam of monochrome light which is reflected by a front surface mirror 112 at an angle $\theta$ of 45° with respect to the surface of a semiconductor wafer 116 which is to be examined. The beam reflected by the mirror 112 is expanded into a broader collimated beam by a conventional beam expander 114. The beam provided by the expander 114 may optionally be polarized by a polarizing filter 115. Alternatively, the filter 115 may be eliminated if a laser 110 is selected which produces a polarized beam.

The beam provided by this system illuminates a portion of the wafer 116. The main part of the beam is reflected out of the field of view of the imaging system as shown by the solid lines. Some of the light rays, however, are scattered as illustrated by the dotted lines. The rays which are scattered in directions about the normal to the wafer surface are collected by a Fourier transform lens 118, located one focal length (f) from the top surface of the wafer 116. This lens generates the Fourier transform of the collimated light reflected from the surface of the wafer 116 at a plane located one focal length behind the lens. This plane is referred to as the Fourier transform plane of the system.

Figure 4A:
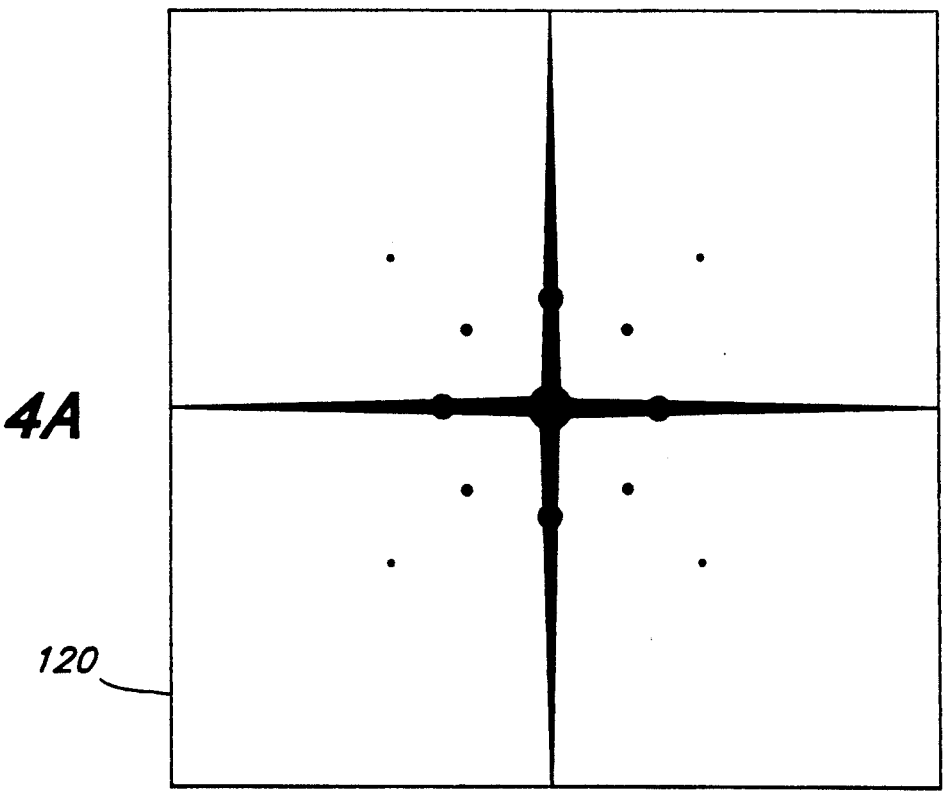
FIG. 4a is an elevation drawing of an exemplary Fourier filter for use in the wafer inspection systems shown in FIGS. 1, 2 and 3.

A Fourier spatial filter 120 is placed at the Fourier transform plane to block the spatial frequency components of the scattered light which correspond to the repeated pattern. An exemplary filter 120 is shown in FIG. 4a. The filter used depends on the spatial frequency components of the pattern to be examined. A suitable spatial filter may be made by placing unexposed photographic film at the Fourier plane and illuminating a sample wafer using the laser 110. The negative of the image at the Fourier plane, obtained by developing the exposed film, may be used as the Fourier filter for wafers which conform to the sample wafer. Alternatively, a spatial light modulator may be used as the spatial filter 120.

The spatially filtered rays provided by the Fourier filter 120 are converted back into a collimated beam by a second lens 122, located one focal length behind the filter 120. This beam forms a dark field image of the illuminated portion of the wafer at the image plane 124, located one focal length behind the lens 122. Magnifying optics 126 increase the size of the image, which is then converted into electrical signals by a conventional video camera 128. The signals from the camera 128 are converted to digital data, which is provided to a computer 130. The computer 130 analyzes the data to discriminate and classify any irregularities in the pattern on the surface of the wafer.

An additional lens element (not shown) may be used to image the Fourier transform plane onto the video camera. This image may then be transferred to the spatial light modulator to configure it as the spatial filter 120. Alternatively, this image may be used to determine the optimal alignment for the photographic Fourier filter.

Figure 1A:
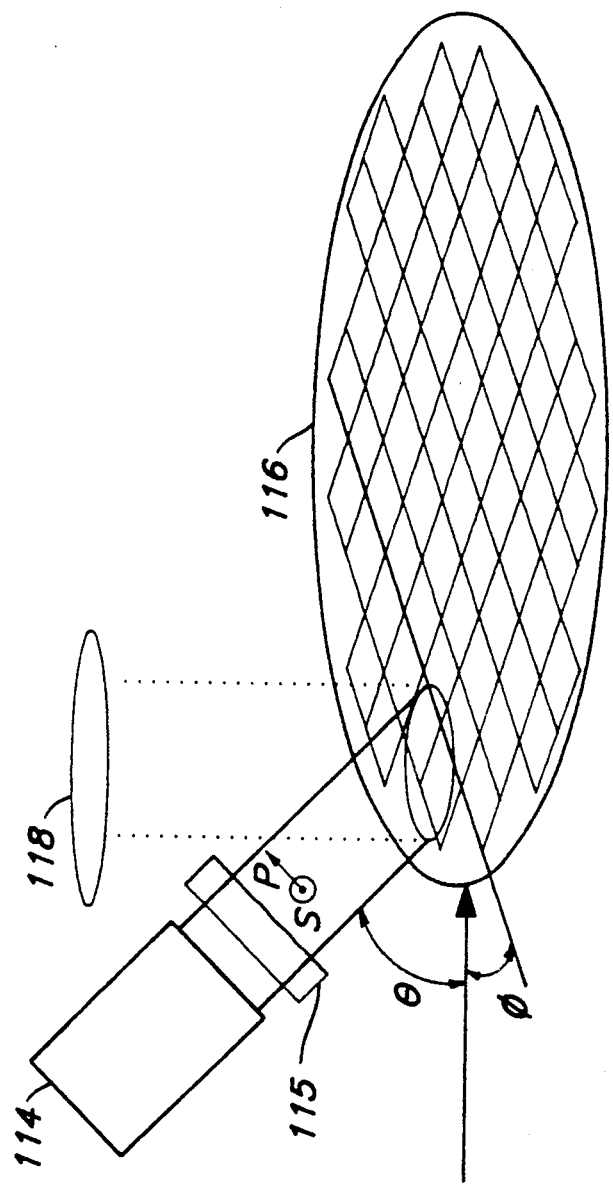
FIG. 1a is a perspective drawing which is useful to describe the manner in which the semiconductor wafer is illuminated by the inspection system shown in FIG. 1.

As shown in FIG. 1a, the wafer 116 is positioned so that the incident beam strikes the surface at an angle, in the plane of the wafer surface, of 45° with respect to the perpendicular lines which predominate in the patterned surface. This angular position is selected to minimize the intensity of the light scattered into the lens system by the pattern.

The system shown in FIG. 1 enhances the defects in the pattern relative to the pattern in several ways. First, the illumination is selected to produce a dark field image and the image is spatially filtered. The dark field imaging technique highlights features on the wafer relative to the background and the spatial filtering strongly attenuates image components having spatial frequencies related to the repetitive pattern.

Figure 4B:
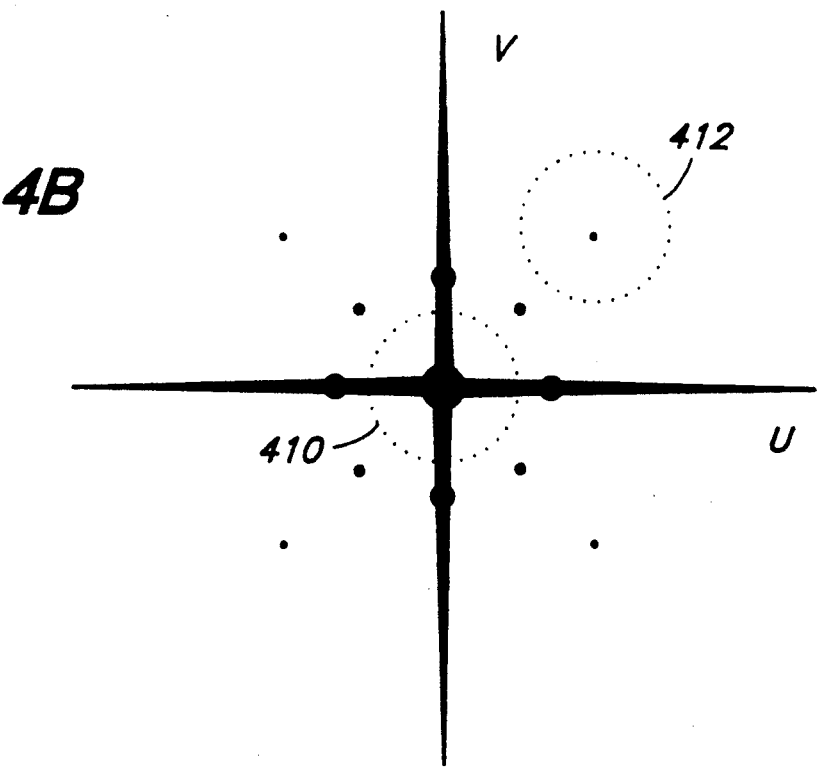
FIG. 4b is a graph of an exemplary spatial frequency spectrum of a semiconductor wafer which is useful for describing the operation of the various embodiments of the invention.

Second, the wafer is illuminated at an incident angle $\theta$ with respect to the surface of the wafer and at an oblique angle $\Phi$ with respect to the pattern lines. The effect of this technique is shown in FIG. 4b. In this Figure, a graph of the Fourier transform of the repetitive pattern is overlaid with two circles representing the viewing numerical aperture, 410, when the wafer is illuminated orthogonal to its surface, and an alternate viewing numerical aperture, 412, when the illumination is displaced from the orthogonal by the angles $\theta$ and $\Phi$. The viewing numerical aperture contains the light which is collected by the system to generate the final image.

As shown in FIG. 4b, when the illumination is orthogonal, a significant portion of the viewing aperture is dominated by the specular beam which corresponds to the zero-order Fourier frequency spectrum of the pattern and the most intense parts of the diffracted beam. These components of the image are blocked by the Fourier filtering techniques used in the bright field imagers such as the above referenced U.S. Pat. No. 4,806,774. This Fourier filter, however, necessarily blocks much of the light in the viewing numerical aperture and, so, produces an image having relatively low contrast.

Conversely, when the illumination source is displaced by the angles $\theta$ and $\Phi$, as in the present invention, the viewing aperture is moved to a relatively empty area of the spatial frequency spectrum. Images obtained through this aperture require less filtering to remove artifacts related to the repetitive pattern. This increases the contrast in the image so that defects in the wafer are accentuated to a greater degree with this system than with a spatially filtered bright field imaging system.

In addition, when the illumination due to the pattern passing through the lens system is decreased in power, the scattering which occurs in each element of the lens system is also decreased. This reduces the level of background light in the dark field image.

Finally, the illumination applied to the wafer may be polarized. Depending on the roughness of the surface features, either p polarization or s polarization may be desirable to further reduce the visibility of pattern features in the dark field image. In most cases s polarization is preferred because low aspect surface roughness is suppressed due to the electromagnetic surface null for s polarization. With some wafers, however, it may be desirable to use p polarization. An example of a wafer of this type is one having trench features etched through a layer of silicon nitride, having a thickness of approximately one-quarter wavelength, which is grown or deposited on a silicon substrate.

Using the system shown in FIG. 1 it is possible to discriminate relatively small particles and defects in the pattern (on the order of 0.34 microns). The system, however, is relatively expensive and difficult to keep in alignment. The systems shown in FIGS. 2 and 3 may be significantly less expensive and easier to use than the system shown in FIG. 1.

Figure 2:
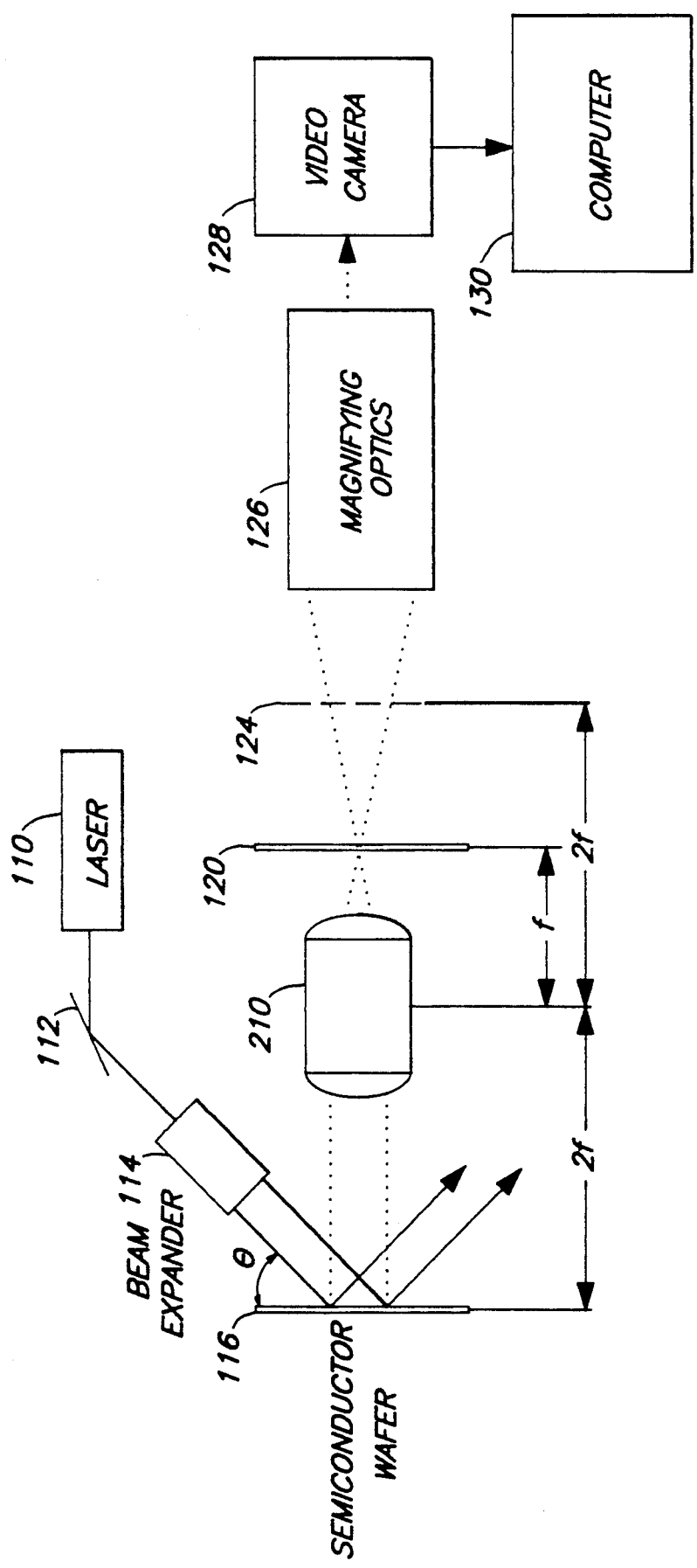
FIGS. 2 and 3 are alternative wafer inspection systems which also include embodiments of the present invention.

The system shown in FIG. 2 is the same as that shown in FIG. 1 except that the two lenses 118 and 122 have been replaced by a single 1:1 lens, 210. The lens 210 is used both as the objective lens to magnify the area being examined and as the Fourier transform lens. When the wafer is placed at two focal lengths (2 f) from the lens 210, an image of the wafer is formed in an image plane located 2 f behind the lens. In addition, a Fourier transform plane exists at a distance of one focal length (f) behind the lens. The performance of this system is equivalent to that of the system shown in FIG. 1 but the number of components in the optical system has been reduced by one.

Figure 3:
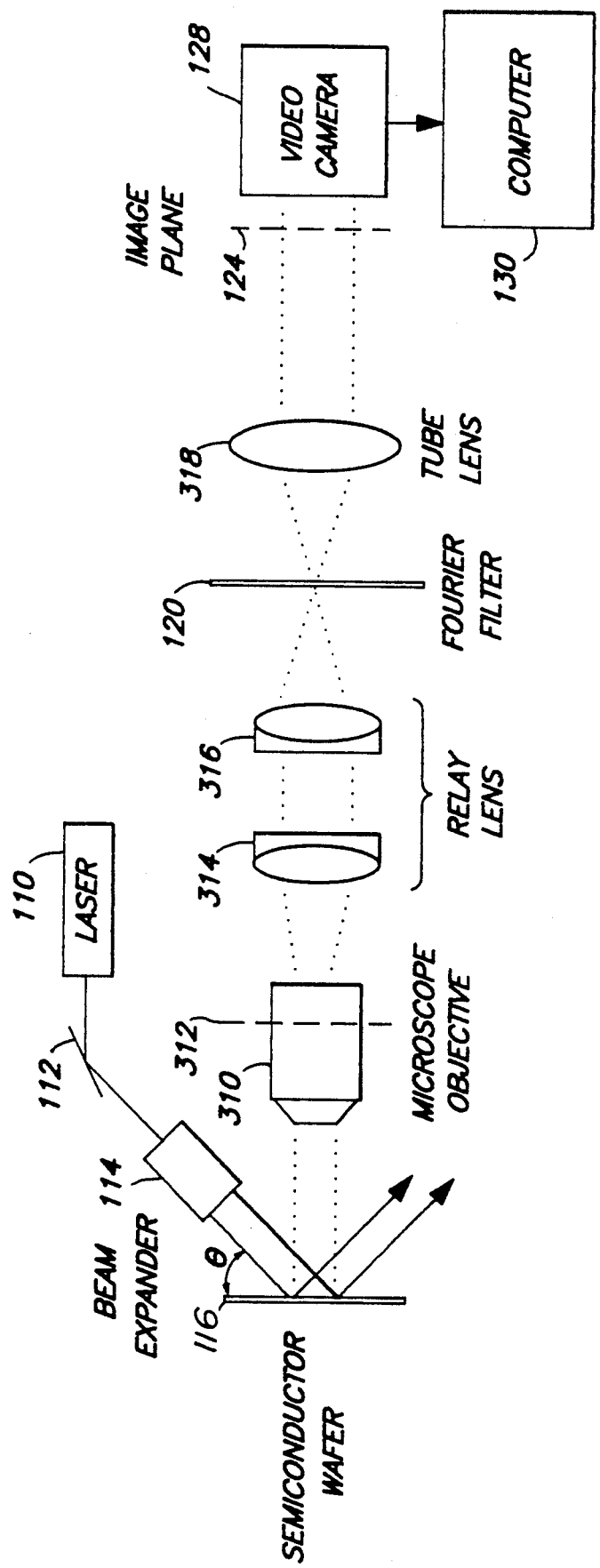

The system shown in FIG. 3 uses a conventional infinity corrected microscope objective 310, an afocal relay lens (314 and 316), such as is commonly used in periscope optical systems, and a tube lens 318 in place of the custom lens 118 the lens 112 and the magnifying optics 126 of the system shown in FIG. 1. While this may increase the parts count of the system, it may also reduce the cost of the system. The microscope objective is likely to be less costly than the custom ground Fourier lens 118 and the tolerances of the relay lens and the tube lens are relaxed relative to the lens 122 and the magnifying optics 126 because the microscope objective magnifies the image of the semiconductor wafer.

The problem with using a microscope objective 310 in a system which performs Fourier spatial filtering is gaining access to the Fourier plane (i.e. the back focal plane 314 of the microscope objective). In many microscope objective lenses, this plane is located inside the objective lens system. The afocal relay lens system 314 and 316 provides an accessible focal plane for the system.

As shown in FIG. 3, the lens 314 is placed at a distance of one focal length from the inaccessible back focal plane of the microscope objective lens 310. The second lens 316 of the relay lens system then forms a Fourier plane at an equivalent distance behind the afocal relay lens system. The Fourier filter 120 is placed at this location.

As set forth above, the exemplary microscope objective lens 310 is an infinity corrected lens. An optical system which uses a lens of this type uses the tube lens 318 to achieve a standard optical tube length of, for example, 160 mm. As described above, in the imaging system shown in FIG. 3, the constraints on the lenses following the microscope objective 310 are relaxed relative to the optical systems used in the other embodiments of the invention. For example, since the image of the wafer is magnified by the microscope objective 310, the resolution requirements of the relay lens system are relaxed (i.e. the relay lenses 314 and 316 do not need to be diffraction limited). In addition, the numerical aperture (NA) of the relay lens system 314, 316 need be only 1/M times that of the objective lens 130 where M is the magnification factor of the lens 130. These lenses should be high quality imaging lenses, however, such as are used in 35 mm cameras, for example.

While all of the described embodiments of the invention have employed a collimated light source, it is contemplated that divergent or convergent light sources may be used when suitable adjustments are made to the optical system to properly align the Fourier transform plane of the image. In addition, it is contemplated that multiple monochromatic light sources may be used instead of the single light source 110. These multiple light sources would produce a larger number of opaque areas on the Fourier filter 120. In another contemplated embodiment, illumination may be applied to the wafer in the four orthogonal directions, in the plane of the wafer surface, which are at 45° degrees with respect to the pattern lines.

In any of the embodiments described above, an illumination mask may be used to block non-repetitive areas of the wafer, such as the kerf areas. In addition, the wafer may be scanned (i.e. moved relative to the remainder of the system) without changing the Fourier pattern, as long as the source of illumination 110 and Fourier filter 120 are held at fixed position. Using this scanning technique, the entire wafer may be examined by the system While the invention has been described in the context of three exemplary embodiments, it is contemplated that it may be practiced as outlined above within the spirit and scope of the appended claims.

The invention claimed is:

1. A method of locating defects on a surface having a repetitive pattern comprising the steps of:
   a) illuminating the surface with a beam of monochrome light at an angle with respect to the surface of the wafer of between 8 degrees and a predetermined maximum angle;
   b) capturing any light which is scattered from the surface at angles greater than the predetermined maximum angle;
   c) spatially filtering the captured light to attenuate spatial frequencies corresponding to the repetitive pattern relative to spatial frequencies corresponding to the defects;
   d) focusing the spatially filtered light into an image, wherein images of the defects are accentuated relative to the image of the repetitive pattern.

2. The method of claim 1 wherein the step a) includes the step of collimating the beam of monochrome light.

3. The method of claim 1 wherein the step a) includes the step of polarizing the beam of monochrome light.

4. The method of claim 1 wherein the surface is planar and the repetitive pattern includes predominantly rectangular features, said step a including the step of orienting the incident beam with respect to the surface at an oblique angle to the rectangular features in the plane of the surface.

5. The method of claim 1 wherein:
   the step c) includes the steps of:
      generating the Fourier transform of the captured light; and
      filtering the Fourier transformed light to attenuate at least one spatial frequency component of the repetitive image; and
   the step d) includes the steps of:
      generating an inverse Fourier transform of the spatially filtered light to produce said image.

6. Apparatus which may be used to locate defects on a surface having a repetitive pattern comprising:
   a) illuminating means for illuminating the surface with at least one beam of monochrome light at a desired angle with respect to the surface of the wafer of between 8 degrees and a predetermined maximum angle;
   b) lens means positioned with an optical axis normal to the surface for capturing light which is scattered from the surface at angles within the numerical aperture of the lens means, wherein the numerical aperture of the lens means defines said predetermined maximum angle;
   c) filtering means for spatially filtering the captured light to attenuate spatial frequencies corresponding to the repetitive pattern relative to spatial frequencies corresponding to the defects; and
   d) imaging means for focusing the spatially filtered light into an image, wherein images of the defects are accentuated relative to the image of the repetitive pattern.

7. The apparatus of claim 6 wherein:
   the illuminating means includes:
      means for generating a beam of monochrome light;
      means for collimating the beam provided by the generating means; and
      means for directing the collimated beam at the surface at the desired angle.

8. The apparatus of claim 7 wherein the illuminating means further includes means for polarizing said collimated beam.

9. The apparatus of claim 6 wherein the filtering means includes:
   Fourier transform means for forming an image representing an optical Fourier transform of the captured light; and
   Fourier filtering means for attenuating portions of said Fourier transform representation corresponding to spatial frequencies exhibited by portions of said captured light corresponding to said repeated pattern relative to other portions of said Fourier transform representation to provide a filtered Fourier Transform representation.

10. The apparatus of claim 9 wherein said Fourier transform means includes a Fourier transform lens.

11. The apparatus of claim 9 wherein said Fourier transform filtering means includes a 1:1 lens positioned at a distance of two focal lengths from said surface to produce said optical Fourier transform representation of said captured light at a distance of one focal length from said 1:1 lens.

12. The apparatus of claim 9 wherein said Fourier transform means includes a microscope objective lens and a relay lens.

13. An apparatus in accordance with claim 12 in which the imaging means includes a tube lens for achieving a desired optical tube length.

14. A method of locating defects on a surface having a repetitive pattern comprising the steps of:
   a) illuminating the surface with a beam of monochrome light at an angle of between 8 and 45 degrees with respect to the surface;
   b) capturing any light which is scattered from the surface at angles between 45 degrees and 90 degrees;
   c) spatially filtering the captured light to attenuate spatial frequencies corresponding to the repetitive pattern relative to spatial frequencies corresponding to the defects;
   d) focusing the spatially filtered light into an image, wherein components of the image representing the defects on the surface are accentuated relative to components of the image representing the repetitive pattern.

15. A method in accordance with claim 14, in which step (a) includes the step of illuminating the surface with a beam of monochrome light at an angle of between 20 and 45 degrees with respect to the surface to accentuate light captured from defects located at and below said surface.

16. A method in accordance with claim 14, in which step (a) includes the step of polarizing the beam of monochrome light to form a p polarized beam, to suppress imaging of trench features below the surface while detecting defects at and below the surface.

* * * * *